US011965200B2

(12) United States Patent
Lee et al.

(10) Patent No.: US 11,965,200 B2
(45) Date of Patent: Apr. 23, 2024

(54) RECOMBINANT MICROORGANISM TRANSFORMED WITH A GLUTARIC ACID TRANSPORTER GENE AND METHOD OF PREPARING GLUTARIC ACID USING SAME

(71) Applicant: KOREA ADVANCED INSTITUTE OF SCIENCE AND TECHNOLOGY, Daejeon (KR)

(72) Inventors: Sang Yup Lee, Daejeon (KR); Tae hee Han, Daejeon (KR)

(73) Assignee: KOREA ADVANCED INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/549,757

(22) Filed: Dec. 13, 2021

(65) Prior Publication Data

US 2022/0205000 A1 Jun. 30, 2022

(30) Foreign Application Priority Data

Dec. 24, 2020 (KR) .................. 10-2020-0183087

(51) Int. Cl.
*C12P 7/44* (2006.01)
*C12N 15/77* (2006.01)
*C12R 1/15* (2006.01)

(52) U.S. Cl.
CPC .............. *C12P 7/44* (2013.01); *C12N 15/77* (2013.01); *C12R 2001/15* (2021.05)

(58) Field of Classification Search
CPC ... C12P 7/44; C12P 7/50; C12N 15/77; C12N 15/52; C12N 9/0008; C12N 9/0069; C12N 9/1096; C12R 2001/15; C07K 14/34; C12Y 102/01024; C12Y 113/12002; C12Y 206/01048
See application file for complete search history.

(56) References Cited

U.S. PATENT DOCUMENTS

2017/0298397 A1* 10/2017 Hara ................. C12N 1/20

FOREIGN PATENT DOCUMENTS

| EP | 0307247 A2 | 3/1989 |
| WO | 9108291 A2 | 6/1991 |

OTHER PUBLICATIONS

Sousa et al., Microbiology 148(Pt5):1291-1303, 2002.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Zhang et al., GenBank accession No. CP022614 published Aug. 10, 2017.*
Shaw-Reid et al., Appl Microbiol Biotechnol 51:325-333, 1999.*
Liu et al., International Journal of Molecular Sciences 22:9065, 2021, pp. 1-17.*
Eikmanns, B.J., et al., "A family of Corynebacterium glutamicum/Escherichia coli shuttle vectors for cloning, controlled gene expression, and promoter probing", Gene, 1991, pp. 93-98, vol. 102, Publisher: Elsevier.
Fothergill, J.C., et al., "Catabolismof L-Lysine by Pseudomonas aeruginosa", Journal of General Microbiology, 1977, pp. 139-155, vol. 99.
Kim, H.T., et al., "Metabolic engineering of Corynebacterium glutamicum for the production of glutaric acid, a C5 dicarbosylic acid platform chemical", Metabolic Engineering, 2018, pp. 99-109, vol. 51.
Lee, P.C., et al., "Batch and continuous cultivation of Anaerobiospirillum succiniciproducens for the production of succinic acid from whey", Appl Microbiol Biotechnol, 2000, pp. 23-27, vol. 54, Publisher: Springer-Verlag.
Lee, P.C., et al., "Succinic Acid Production with Reduced By-Product Formation in the Fermentation of Anaerobiospirillum succiniciproducens Using Glycerol as a Carbon Source", Biotechnol. Bioeng., 2001, pp. 42-48, vol. 72, Publisher: John Wiley & Sons, Inc.
Lee, P.C., et al., "Isolation and characterization of a new succinic acid-producing bacterium, Mannheimia succiniciproducens MBEL55E, from bovine rumen", Appl Microbiol Biotechnol, 2002, pp. 663-668, vol. 58.
Lee, P.C., et al., "Batch and continuous cultures of Mannheimia succiniciproducens MBEL55E for the production of succinic acid from whey and corn steep liquor", Bioprocess Biosyst Eng, 2003, pp. 63-67, vol. 26.
Lee, P.C., et al., "Biological conversion of wood hydrolysate to succinic acid by Anaerobiospirillum succiniciproducens", Biotechnology Letters, 2003, pp. 111-114, vol. 25, Publisher: Kluwer Academic Publishers.
Lubitz, D., et al., "Roles of export genes cgmA and lysE for the production of L-arginine and L-citrulline by Corynebacterium glutamicum", Applied Microbial Biotechnol, 2016, pp. 8465-8474, vol. 100, Publisher: Springer.

(Continued)

*Primary Examiner* — Delia M Ramirez
(74) *Attorney, Agent, or Firm* — HULTQUIST, PLLC; Steven J. Hultquist

(57) ABSTRACT

The present invention relates to a recombinant microorganism imparted with increased ability to produce glutaric acid by further introducing a gene encoding a polypeptide having glutaric acid transporter activity into a microorganism having ability to produce glutaric acid, and to a method of preparing glutaric acid using the recombinant microorganism. According to the present invention, glutaric acid used for the preparation of various compounds such as polyamide, polyurethane, 1,5-pentanediol, and 5-hydroxyvaleric acid can be biosynthesized at high yield.

2 Claims, 4 Drawing Sheets

Specification includes a Sequence Listing.

(56) References Cited

OTHER PUBLICATIONS

Park, S.J., et al., "Metabolic engineering of *Escherichia coli* for the production of 5-aminovalerate and glutarate as C5 platform chemicals", Metabolic Engineering, 2013, pp. 42-27, vol. 16, Publisher: Elsevier.

Park, S.H., et al., "Metabolic engineering of Corynebacterium glutamicum for L-arginine production", Nature communications, Aug. 5, 2014, Page(s) DOI:10.1038/NCOMMS5618, Publisher: Macmillan Publishers Limited.

Rohles, C.M., et al., "A bio-based route to the carbon-5 chemical glutaric acid and to bionylon-6,5 using metabolically engineered Corynebacterium glutamicum", Green Chemistry, 2018, pp. 4662-4674, vol. 20, Publisher: The Royal Society of Chemistry.

Shin, J.H., et al., "Metabolic engineering of Corynebacterium glutamicum for enhanced production of 5-aminovaleric acid", Microbial Cell Factories, 2016, Page(s) DOI:10.1186/s12934-016-0566-8, vol. 15, No. 174, Publisher: BioMed Central.

Wang, J., et al., "De Novo Biosynthesis of Glutarate via -Keto Acid Carbon Chain Extension and Decarboxylation Pathway in *Escherichia coli*", ACS Synthetic Biology, 2017, pp. 1922-1930, vol. 6, Publisher: ACS Publications.

Youn, J-W, et al., "Characterization of he Dicarboxylate Transporter DctA in Corynebacterium glutamicum", Journal of Bacteriology, 2009, pp. 5480-5488, vol. 191, No. 17, Publisher: American Society for Microbiology.

Office Action Issued in Chinese Patent Application No. 202111587989.7 dated Jul. 20, 2023.

English Translation of Office Action Issued in Chinese Patent Application No. 202111587989.7 dated Jul. 20, 2023.

Search Report Issued in Chinese Patent Application No. 202111587989.7 dated Jul. 20, 2023.

Cornebacterium glutamicum strain BE chromosome, complete genome, CP053189.1 , NCBI.

Multispecies: MFS transporter (Corynebacterium) NCBI Reference Sequence: WP_044394987.1.

* cited by examiner

RECOMBINANT MICROORGANISM TRANSFORMED WITH A GLUTARIC ACID TRANSPORTER GENE AND METHOD OF PREPARING GLUTARIC ACID USING SAME

CROSS-REFERENCE TO RELATED APPLICATION

The priority under 35 USC § 119 of Korean Patent Application 10-2020-0183087 filed Dec. 24, 2020 for RECOMBINANT MICROORGANISM INTRODUCED WITH GLUTARIC ACID TRANSPORTER GENE AND METHOD OF PREPARING GLUTARIC ACID USING SAME is hereby claimed. The disclosure of Korean Patent Application 10-2020-0183087 is hereby incorporated herein by reference, in its entirety, for all purposes.

Reference to Sequence Listing Submitted Via EFS-Web

This application includes an electronically submitted sequence listing in .txt format. The .txt file contains a sequence listing entitled "610_SeqListing_ST25.txt" created on Dec. 13, 2021 and is 21,327 bytes in size. The sequence listing contained in this .txt file is part of the specification and is hereby incorporated by reference herein in its entirety.

TECHNICAL FIELD

The present invention relates to a recombinant microorganism having improved ability to produce glutaric acid, and more particularly to a recombinant microorganism imparted with increased ability to produce glutaric acid by further introducing a gene encoding a polypeptide having glutaric acid transporter activity into a microorganism having ability to produce glutaric acid, and a method of preparing glutaric acid using the recombinant microorganism.

BACKGROUND ART

With the increased concern over climate change and reliance on fossil resources, thorough research is ongoing into bio-based production of chemicals, fuels and materials from renewable resources. Among various high-value-added compounds, bio-based polymers and monomers are receiving great attention as eco-friendly alternatives to petroleum-derived plastics. Glutaric acid, also known as pentanedioic acid, is a material widely used in the preparation of various compounds including polyester, polyamide, polyurethane, 1,5-pentanediol, and 5-hydroxyvaleric acid. Glutaric acid is produced through various petroleum-based chemical methods, including oxidation of 2-cyanocyclopentanone using nitric acid as a catalyst and condensation of ethyl malonate and acrylonitrile. However, this process is disadvantageous due to the use of nonrenewable and toxic materials. Therefore, various approaches have been proposed for biological production of glutaric acid from renewable resources.

Glutaric acid is a naturally occurring metabolite of the catabolism of lysine in *Pseudomonas* species, in which lysine is converted into glutaric acid via a 5-aminovaleric acid (AVA) pathway (Fothergill et al., *J. Gen. Microbiol.* 99, 139-155, 1977). Previously, the production of glutaric acid in *E. coli* using this pathway including the davB, davA, davT, and davD genes encoding L-lysine 2-monooxygenase (DavB), 5-aminovaleramide amidohydrolase (DavA), aminovalerate aminotransferase (DavT), and glutarate semialdehyde dehydrogenase (DavD), respectively, was reported for the first time (Park et al., *Metab. Eng.* 16, 42-47, 2013). In addition, although use of a pathway involving condensation of α-ketoglutarate and acetyl-CoA was attempted in *E. coli*, the titer of glutaric acid obtained through flask culture was only 0.42 g/L (Wang et al., *ACS Synth. Biol.* 6, 1922-1930, 2017). Production of glutaric acid using metabolically engineered *Corynebacterium glutamicum* has also been reported in several studies (Shin et al., *Microb. Cell Fact.* 15, 174, 2016, Rohles et al., *Green Chem.* 20, 4662-4674, 2018, Kim et al., *Metab. Eng.* 51, 99-109, 2019). A recombinant *Corynebacterium glutamicum* strain that mass-produces glutaric acid by manipulating the production strain of AVA, which is a glutaric acid precursor, has been reported (Rohles et al., *Green Chem.* 20, 4662-4674, 2018). This recombinant strain, which overexpresses genes encoding 5-aminovalerate aminotransferase (GabT), succinate-semialdehyde dehydrogenase (GabD), and AVA transporter (Ncg10464), produced 90 g/L of glutaric acid.

Upon overproduction of a desired compound using a recombinant microorganism, efficient transport is essential so that the compound may be continuously synthesized in the cell. Various studies have demonstrated that overexpression of a transporter of a target material increases the biological production thereof (Rohles et al., *Green Chem.* 20, 4662-4674, 2018, Lubitz et al., *J. Appl. Microbiol.* 100, 8465-8474, 2016, Youn et al., *J. Bacteriol.* 191, 5480-5488, 2009). However, no glutaric acid transporter for *Corynebacterium glutamicum* has been reported yet.

Accordingly, the present inventors have made great efforts to develop methods of efficiently transporting glutaric acid produced from recombinant *Corynebacterium glutamicum* and consequently improving the ability to produce glutaric acid, and thus newly identified a gene encoding a polypeptide having glutaric acid transporter activity and ascertained that the production of glutaric acid is improved in the recombinant microorganism having the ability to produce glutaric acid into which the above gene is introduced, thus culminating in the present invention.

DISCLOSURE

Technical Problem

It is an object of the present invention to provide a recombinant microorganism having improved ability to produce glutaric acid.

It is another object of the present invention to provide a method of preparing glutaric acid using the recombinant microorganism.

Technical Solution

In order to accomplish the above objects, the present invention provides a recombinant microorganism imparted with increased ability to produce glutaric acid by further introducing a ynfM gene into a microorganism having ability to produce glutaric acid.

In addition, the present invention provides a method of preparing glutaric acid, including:

(a) producing glutaric acid by culturing the recombinant microorganism described above; and (b) recovering the produced glutaric acid.

Advantageous Effects

According to the present invention, glutaric acid used for the preparation of various compounds such as polyester, polyamide, polyurethane, 1,5-pentanediol, and 5-hydroxyvaleric acid can be biosynthesized at high yield.

MODE FOR INVENTION

Unless otherwise defined, all scientific terms used herein have the same meanings as those typically understood by those skilled in the art to which the present invention belongs. Generally, the nomenclature used herein is typical in the art.

Figure 1:
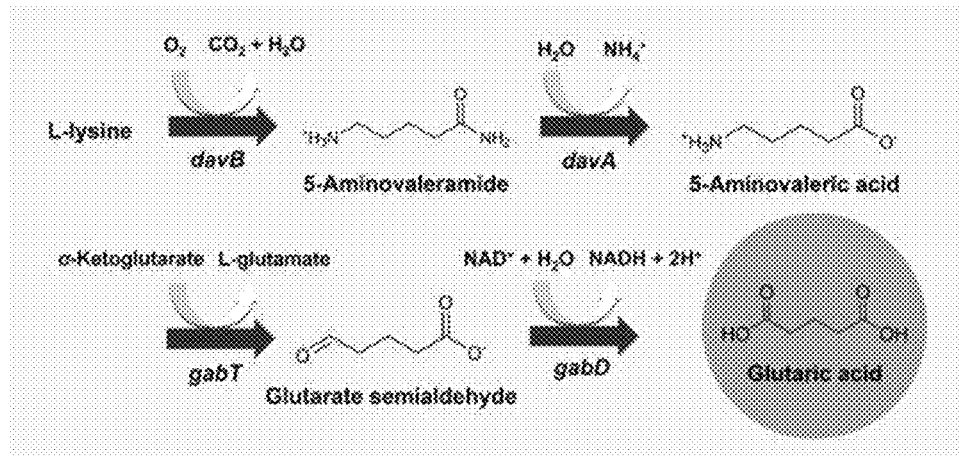
FIG. 1 schematically shows a pathway for biosynthesis of glutaric acid from lysine.

Glutaric acid is a compound used for the preparation of various compounds such as polyurethane, 1,5-pentanediol and 5-hydroxyvaleric acid. Chemical synthesis methods have conventionally been used therefor, and recently, glutaric acid has been prepared using a recombinant microorganism through a glutaric acid biosynthesis pathway (FIG. 1), but the transporter of glutaric acid accumulating in cells has not been identified, so the ability of the recombinant microorganism to produce glutaric acid is low. In the present invention, a gene having glutaric acid transporter activity is identified, and it is also confirmed that the recombinant microorganism using the gene having glutaric acid transporter activity and the glutaric acid biosynthesis pathway exhibits high ability to produce glutaric acid compared to a recombinant microorganism into which no gene having glutaric acid transporter activity is introduced.

Accordingly, an aspect of the present invention pertains to a recombinant microorganism having increased ability to produce glutaric acid, in which a gene encoding a polypeptide having glutaric acid transporter activity is additionally introduced into a microorganism having ability to produce glutaric acid.

In the present invention, a glutaric acid transporter is defined as a glutaric acid permease capable of transporting glutaric acid to the outside of the cell.

In the present invention, the gene encoding the polypeptide may be selected from the group consisting of a ynfM gene, a yjjP gene, a yjjB gene, a yeeA gene, and a sucE1 gene.

In the present invention, the ynfM gene may be a gene encoding a polypeptide represented by SEQ ID NO: 1, and the ynfM gene may be represented by SEQ ID NO: 2.

Figure 6:
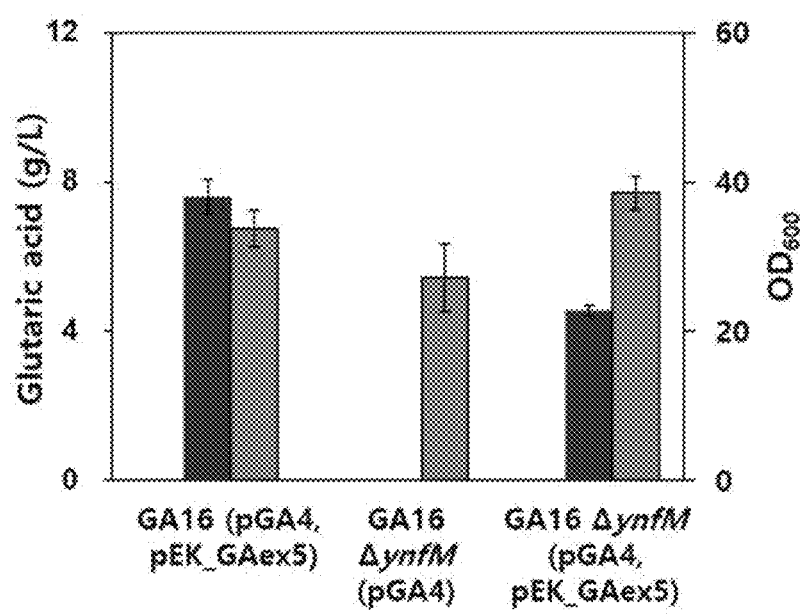
FIG. 6 shows the results of confirming the ability to produce glutaric acid in *Corynebacterium glutamicum* in which the gene encoding the glutaric acid transporter is deleted from the genome.

In an embodiment of the present invention, a recombinant strain GA16ΔynfM in which the ynfM gene is knocked out from the chromosomal DNA of *Corynebacterium glutamicum* GA16 is constructed, and a pEK_GAex5 vector for overexpression of the ynfM gene and a pGA4 vector are introduced into the GA16ΔynfM strain in which the ynfM gene is knocked out, thus constructing a GA16ΔynfMI (pGA4, pEK_GAex5) strain in which the recombinant microorganism subjected to gene knockout is transformed with the pEK_GAex5 vector in order to confirm the effect of restoring the expression of the ynfM gene. Based on the results of measurement of the ability of the recombinant strains thus constructed to produce glutaric acid, glutaric acid was not produced at all in the recombinant strain in which the ynfM gene was knocked out, whereas the recombinant strain in which the expression of the ynfM gene was restored through introduction of the recombinant vector was confirmed to produce 4.6 g/L of glutaric acid (FIG. 6). Therefore, it was demonstrated that the *Corynebacterium glutamicum* Ncg12828 (ynfM) gene has glutaric acid transporter activity.

In the present invention, the microorganism having the ability to produce glutaric acid may be a microorganism having increased ability to produce lysine.

In an embodiment of the present invention, used as the microorganism having increased ability to produce lysine may be a recombinant microorganism in which the start codon of the icd gene is changed, the ddh gene is further introduced, the promoters of the dapB gene, dapA gene, ppc gene and lysA gene are substituted with strong promoters, and the lysE gene is deleted.

In the present invention, the microorganism having the ability to produce glutaric acid may include a gene selected from the group consisting of a davA gene, a davB gene, a gabT gene, and a gabD gene.

Examples of the microorganism strain usable in the present invention may include bacteria, archaea, yeast, mold, protozoa (flagellate, amoeba, choanoflagellate, Rhizaria, Chromalveolata), animal cells, microalgae, plant cells, and the like. Preferable examples thereof include *Escherichia coli, Bacillus* sp., *Corynebacterium* sp., *Lactobacillus* sp., *Lactococcus* sp., *Pseudomonas* sp., *Anacystis* sp., *Anabaena* sp., *Chlorobium* sp., *Chloroflexus* sp., *Clostridium* sp., *Methanobacterium* sp., *Propionibacterium* sp., *Rhodopseudomonas* sp., *Rhodobacter* sp., *Rhodovulum* sp., *Streptococcus* sp., *Saccharomyces* sp., *Aspergillus* sp., *Arabidopsis* sp., *Glycine* sp., *Nicotiana* sp., *Zea* sp., and the like, and particularly preferred examples thereof include *Escherichia coli, Bacillus subtilis, Corynebacterium glutamicum, Lactobacillus brevis, Lactobacillus casei, Lactobacillus reuteri, Lactococcus lactis, Aspergillus niger, Saccharomyces cerevisiae, Saccharomyces pombe*, and the like, but the present invention is not limited thereto.

In the present invention, the process of culturing the mutant microorganism may be performed using a commonly known culture method, and in addition to the specific medium and specific culture method used in the embodiment of the present invention, whey, saccharification solutions such as CSL (corn steep liquor), etc., and other media may be used, and various methods such as fed-batch culture, continuous culture and the like may be carried out (Lee et al., *Bioprocess Biosyst. Eng.*, 26: 63, 2003; Lee et al., *Appl. Microbiol. Biotechnol.*, 58: 663, 2002; Lee et al., *Biotechnol. Lett.*, 25: 111, 2003; Lee et al., *Appl. Microbiol. Biotechnol.*, 54: 23, 2000; Lee et al., *Biotechnol. Bioeng.*, 72: 41, 2001).

As used herein, the term "vector" refers to a nucleic acid molecule containing a DNA sequence operably linked to a suitable expression control sequence capable of expressing DNA in a suitable host. The vector may be a plasmid, a phage particle, or a potential genomic insert. Upon transformation into an appropriate host, the vector may replicate and function independently of the host genome, or in some cases may be integrated into the genome itself.

Since a plasmid is currently the most commonly used form of vector, "plasmid" and "vector" are sometimes used interchangeably in the context of the present invention. However, the present invention includes other forms of vectors having functions equivalent to those known or becoming known in the art. Typical expression vectors for expression of a mammalian cell culture are based on, for example, pRK5 (EP 307,247), pSV16B (WO 91/08291), and pVL1392 (Pharmingen).

The phrase "expression control sequence" refers to a DNA sequence that is essential for the expression of an operably linked coding sequence in a certain host organism. Such a control sequence includes a promoter for transcription, an arbitrary operator sequence for regulating such transcription, a sequence encoding a suitable mRNA ribosome-binding site, and a sequence for regulating termination of transcription and translation. For example, a control sequence suitable for prokaryotes includes a promoter, an arbitrary operator sequence, and a ribosome-binding site. A eukaryotic cell includes a promoter, a polyadenylation signal, and an enhancer. The factor that most affects the expression level of a gene in the plasmid is a promoter. Preferred examples of the promoter for high expression include a SRα promoter and a cytomegalovirus-derived promoter.

In order to express the DNA sequence of the present invention, any of a wide variety of expression control sequences may be used in the vector. Examples of useful expression control sequences include early and late promoters of SV40 or adenovirus, lac system, trp system, TAC or TRC system, T3 and T7 promoters, major operator and promoter regions of phage lambda, fd coding protein control regions, promoters for 3-phosphoglycerate kinase or other glycolytic enzymes, phosphatase promoters, such as Pho5, promoters of yeast alpha-mating systems, and other constitutive and inducible sequences known to control the expression of genes in prokaryotic or eukaryotic cells or viruses thereof, and various combinations thereof. The T7 RNA polymerase promoter Φ10 may be useful in the expression of proteins in E. coli.

A nucleic acid is said to be "operably linked" when placed in a functional relationship with another nucleic acid sequence. It may be a gene and control sequence(s) linked in such a manner that an appropriate molecule (e.g. a transcriptional activation protein), when bound to the control sequence(s), allows for gene expression. For example, DNA for a pre-sequence or secretory leader is operably linked to DNA for a polypeptide when expressed as a preprotein that participates in secretion of the polypeptide, a promoter or enhancer is operably linked to a coding sequence when affecting the transcription of the sequence, a ribosome-binding site is operably linked to a coding sequence when affecting the transcription of the sequence, or a ribosome-binding site is operably linked to a coding sequence when positioned to facilitate translation. In general, "operably linked" means that the linked DNA sequence is in contact therewith, and also that the secretory leader is in contact therewith and is present in the reading frame. However, the enhancer need not be in contact therewith. Linkage of these sequences is accomplished by ligation at convenient restriction enzyme sites. When no such site exists, a synthetic oligonucleotide adapter or linker according to a typical method is used.

As used herein, the term "expression vector" generally refers to a double-stranded DNA fragment as a recombinant carrier into which a heterologous DNA fragment is inserted. Here, heterologous DNA is hetero DNA, which is DNA not found naturally in a host cell. An expression vector, once in the host cell, is able to replicate independently of the host chromosomal DNA, and several copies of the vector and inserted (heterologous) DNA thereof may be produced.

As is well known in the art, in order to increase the expression level of a transfected gene in a host cell, the corresponding gene has to be operably linked to the transcriptional and translational expression control sequence that functions in the selected expression host. Preferably, the expression control sequence and the corresponding gene are contained in a single expression vector including both the bacterial selection marker and the replication origin. When the expression host is a eukaryotic cell, the expression vector has to further include an expression marker useful in the eukaryotic expression host.

In the present invention, a wide variety of expression host/vector combinations may be used to express the DNA sequence of the protein of interest. Expression vectors suitable for eukaryotic hosts include, for example, expression control sequences derived from SV40, bovine papillomavirus, adenovirus, adeno-associated virus, cytomegalovirus, and retrovirus. Expression vectors that may be used in bacterial hosts include bacterial plasmids, exemplified by those obtained from E. coli, such as pBlueScript, pGEX2T, pUC vector, col E1, pCR1, pBR322, pMB9 and derivatives thereof, plasmids useful across a wide host range, such as RP4, phage DNA exemplified by a wide variety of phage lambda derivatives, such as Agt10, λgt11, and NM989, and other DNA phages, such as M13 and filamentous single-stranded DNA phages. The expression vectors useful for yeast cells are 2 μ plasmids and derivatives thereof. A useful vector for insect cells is pVL 941.

A host cell transformed or transfected with the above-described expression vector constitutes another aspect of the present invention. As used herein, the term "transformation" refers to the introduction of DNA into a host such that the DNA becomes replicable either as an extrachromosomal factor or through chromosomal integration. As used herein, the term "transfection" means that an expression vector is accepted by a host cell, regardless of whether or not any coding sequence is actually expressed.

A host cell of the invention may be a prokaryotic or eukaryotic cell. In addition, a host having high DNA introduction efficiency and high expression efficiency of the introduced DNA is commonly used. Examples of the host cell that may be used may include well-known eukaryotic and prokaryotic hosts such as E. coli, Pseudomonas, Bacillus, Streptomyces, fungi, and yeast, insect cells such as Spodoptera frugiperda (SF9), animal cells such as CHO and mouse cells, African green monkey cells such as COS 1, COS 7, BSC 1, BSC 40 and BMT 10, and tissue-cultured human cells. When cloning cDNA encoding the protein of the present invention, it is preferable to use an animal cell as a host. In the present invention, CHSE-214, FHM, RTG-2 and EPC of piscine origin are examples, but the present invention is not limited thereto. In the case of using COS cells, since SV40 large T antigen is expressed in COS cells, the plasmid having the replication origin of SV40 exists as multiple copies of an episome in the cell, and higher expression thereof may be expected. The introduced DNA sequence may be obtained from the same species as the host cell, may be of a different species from the host cell, or may be a hybrid DNA sequence including any heterologous or homologous DNA.

It should be naturally understood that not all vectors and expression control sequences function equally in expressing the DNA sequences of the present invention. Likewise, not all hosts function equally in the same expression system. However, those skilled in the art may make appropriate selection from among various vectors, expression control sequences, and hosts without departing from the scope of the present invention without undue experimental burden. For example, in selecting a vector, the host has to be taken into consideration. This is because the vector has to be replicated therein. The number of copies of the vector, the ability thereof to control the number of copies, and the expression of other proteins encoded by the vector, for example antibiotic markers, also have to be taken into consideration. In selecting the expression control sequence, various factors have to be taken into consideration. For example, the relative strength of sequences, the likelihood of control thereof, and compatibility with DNA sequences of the present invention, etc., should be taken into account, particularly with regard to possible secondary structures. The single-cell host should be selected in consideration of factors such as the selected vector, the toxicity of the product encoded by the DNA sequence of the present invention, the secretory properties, the ability to correctly fold the protein, culture and fermentation requirements, and ease of purification of the product encoded by the DNA sequence of the present invention from the host. Within the scope of these factors, those skilled in the art may select various combinations of vectors, expression control sequences, and hosts capable of expressing the DNA sequences of the present invention in fermentation or large-scale animal culture. As a screening method for cloning cDNA of the protein through expression cloning, a binding method, a panning method, a film emulsion method, etc. may be applied.

In the present invention, "gene-codon-optimized sequence" and "codon optimization" used in the present invention refer to substitution of some amino acid codons among amino acid codons encoding a target material so that the expression level of a material encoded by a specific gene increases depending on the type of host cell. Various combinations and applications of substitutions of some amino acid codons will be possible by those skilled in the art.

Another aspect of the present invention pertains to a method of preparing glutaric acid, including:

(a) producing glutaric acid by culturing the recombinant microorganism of the present invention; and (b) recovering the produced glutaric acid.

In an embodiment of the present invention, a *Corynebacterium glutamicum* GA16 strain into which a pGA4 vector, which is a recombinant vector for glutaric acid biosynthesis including a davA gene, a davB gene, a gabT gene and a gabD gene, and a pEK_GAex5 vector, which is a recombinant vector for overexpression of a ynfM gene, are introduced was constructed, and the ability of the strain to produce glutaric acid was measured. As a result, 6.5 g/L of glutaric acid was produced in the control recombinant strain transformed with the empty vector, and 7.6 g/L of glutaric acid was produced in the recombinant strain transformed with the pEK_GAex5 vector containing the ynfM gene, indicating that production of glutaric acid was increased due to overexpression of the glutaric acid transporter gene.

EXAMPLES

A better understanding of the present invention may be obtained through the following examples. These examples are merely set forth to illustrate the present invention, and are not to be construed as limiting the scope of the present invention, as will be apparent to those skilled in the art.

Example 1: Construction of Recombinant Strain Having Increased Ability to Produce Lysine In this example, a recombinant *Corynebacterium glutamicum* strain having increased ability to produce lysine as a glutaric acid precursor was conducted.

The following genetic manipulation was performed in the genome of the *Corynebacterium glutamicum* BE strain (*C. glutamicum* KCTC 12390BP): change of the start codon of the icd gene, further introduction of the ddh gene, promoter substitution of the dapB gene, dapA gene, ppc gene and lysA gene, and deletion of the lysE gene.

1-1: Change of Start Codon of Icd Gene

Genes were manipulated through previously reported methods (Park S. H. et al., Nat. Commun. 5, 4618, 2018). In order to change the start codon of the icd gene from atg into gtg, the upstream portion, which is the homologous arm, was amplified in the *C. glutamicum* BE genome using the primers of SEQ ID NO: 3 and SEQ ID NO: 4, and the downstream portion was amplified in the *C. glutamicum* BE genome using the primers of SEQ ID NO: 5 and SEQ ID NO: 6. Then, the amplified sequences were inserted into pK19mob-sacB cleaved with BamHI and PstI through Gibson assembly, thereby constructing a final vector psacB_icd.

```
SEQ ID NO: 3:
GCCAAGCTTGCATGCCTGCAGGAATCTGCAGACCACTCGCC

SEQ ID NO: 4:
AAGGAGACTCGTGGCTAAGATCATCTGGACCC

SEQ ID NO: 5:
TCTTAGCCACGAGTCTCCTTGGTTGATGGGC

SEQ ID NO: 6:
ATTCGAGCTCGGTACCCGGGGATCCGCACGCATCCTCGAAGACC
```

1-2: Further Introduction of Ddh Gene

For further introduction of the ddh gene, the upstream portion, which is the homologous arm, was amplified in the *C. glutamicum* BE genome using the primers of SEQ ID NO: 7 and SEQ ID NO: 8, and the downstream portion was amplified in the *C. glutamicum* BE genome using the primers of SEQ ID NO: 9 and SEQ ID NO: 10. Then, the amplified sequences were inserted into pK19mob-sacB cleaved with BamHI and PstI through Gibson assembly, thereby constructing a final vector psacB_icd.

```
SEQ ID NO: 7:
GCCAAGCTTGCATGCCTGCAGTCGTGGTCTGGTCCACGG

SEQ ID NO: 8:
CAGACCACGACATCCAAACCCAACCGCG

SEQ ID NO: 9:
GGTTTGGATGTCGTGGTCTGGTCCACGG

SEQ ID NO: 10:
ATTCGAGCTCGGTACCCGGGGATCCCATCCAAACCCAACCGCG
```

1-3: Promoter Substitution of dapB Gene, dapA Gene, Ppc Gene and lysA Gene

For promoter substitution of the dapB, dapA, ppc, and lysA genes, the upstream portion, which is the homologous arm, was amplified in the *C. glutamicum* BE genome using the primer pairs of SEQ ID NOS: 11 and 12, SEQ ID NOS:

17 and 18, SEQ ID NOS: 23 and 24, and SEQ ID NOS: 29 and 30, respectively, and the downstream portion was amplified in the *C. glutamicum* BE genome using the primer pairs of SEQ ID NOS: 15 and 16, SEQ ID NOS: 21 and 22, SEQ ID NOS: 27 and 28, and SEQ ID NOS: 33 and 34, respectively. An H36 promoter to be substituted was amplified in the pCES208s vector using the primer pairs of SEQ ID NOS: 13 and 14, SEQ ID NOS: 19 and 20, SEQ ID NOS: 25 and 26, and SEQ ID NOS: 31 and 32. Then, the amplified sequences were inserted into pK19mob-sacB cleaved with BamHI and PstI through Gibson assembly, thereby constructing final vectors psacB_36dapB, psacB_36dapA, psacB_36ppc, and psacB_36lysA.

```
Primers for construction of psacB_36dapB
SEQ ID NO: 11:
GCCAAGCTTGCATGCCTGCAGTCTGGCTGTGCGTCCATG

SEQ ID NO: 12:
CATGGGATCCATGGGAATCAAGGTTGGCGTTC

SEQ ID NO: 13:
CTTGATTCCCATGGATCCCATGCTACTCCTACC

SEQ ID NO: 14:
CTTAAGTCTCATGGTACCTCTATCTGGTGCCC

SEQ ID NO: 15:
TAGAGGTACCATGAGACTTAAGTTGCCCTTCACC

SEQ ID NO: 16:
ATTCGAGCTCGGTACCCGGGGATCCCCTTGAATATTGACGTT

GAGGAAGGAATC

Primers for construction of psacB 36dapA
SEQ ID NO: 17:
GCCAAGCTTGCATGCCTGCAGACGAGGTCACCCTTGGCG

SEQ ID NO: 18:
CATGGGATCCATGAGCACAGGTTTAACAGCTAAGAC

SEQ ID NO: 19:
ACCTGTGCTCATGGATCCCATGCTACTCCTACC

SEQ ID NO: 20:
ATGGACTTTTAAGGTACCTCTATCTGGTGCCC

SEQ ID NO: 21:
TAGAGGTACCTTAAAAGTCCATGACATACGGGCTTG

SEQ ID NO: 22:
ATTCGAGCTCGGTACCCGGGGATCCCCGAGGCATTTCTCGGTCC

Primers for construction of psacB_36ppc
SEQ ID NO: 23:
GCCAAGCTTGCATGCCTGCAGGGTAGGCTCCGCAGACTG

SEQ ID NO: 24:
CATGGGATCCATGACTGATTTTTTACGCGATGACATC

SEQ ID NO: 25:
AAAATCAGTCATGGATCCCATGCTACTCCTAC

SEQ ID NO: 26:
GTAGAAGTGCGGGGTACCTCTATCTGGTGCC

SEQ ID NO: 27:
TAGAGGTACCCCGCACTTCTACAGTGCTTG

SEQ ID NO: 28:
ATTCGAGCTCGGTACCCGGGGATCCCTGCTCTTGGGTTGTCGTTG

Primers for construction of psacB_36lysA
SEQ ID NO: 29:
GCCAAGCTTGCATGCCTGCAGCGTTCCTCCGTGGATTCCTC

SEQ ID NO: 30:
TAGAGGTACCTGTTACATCTTCTCCGGTGCG

SEQ ID NO: 31:
GAAGATGTAACAGGTACCTCTATCTGGTGCCC

SEQ ID NO: 32:
AACTGTAGCCATGGATCCCATGCTACTCCTACC

SEQ ID NO: 33:
CATGGGATCCATGGCTACAGTTGAAAATTTCATGACTTCC

SEQ ID NO: 34:
AGTGATTCGAGCTCGGTACCCGGGGCTTTACGCGGATCAACAC
```

1-4: Deletion of lysE Gene

For deletion of the lysE gene, the upstream portion, which is the homologous arm, was amplified in the *C. glutamicum* BE genome using the primer pair of SEQ ID NOS: 35 and 36, and the downstream portion was amplified in the *C. glutamicum* BE genome using the primer pair of SEQ ID NOS: 37 and 38. Then, the amplified sequences were inserted into pK19mob-sacB cleaved with BamHI and PstI through Gibson assembly, thereby constructing a final vector psacB_lysE2.

```
SEQ ID NO: 35:
GCTTGCATGCCTGCAATCTGCTGCAGTCAGCTGCC

SEQ ID NO: 36:
GTCTGCTTTGCGACACCGGACGGTGGATTTTC

SEQ ID NO: 37:
GGTGTCGCAAAGCAGACCTGTAATGAAGATTTCCATG

SEQ ID NO: 38:
AGCTCGGTACCCGGGCATCAACCATGTAGGCATCCCG
```

The recombinant strain having increased ability to produce lysine constructed as described above was named GA16, and was used as a recombinant microorganism for the production of glutaric acid in Examples 4 and 5.

Figure 2:
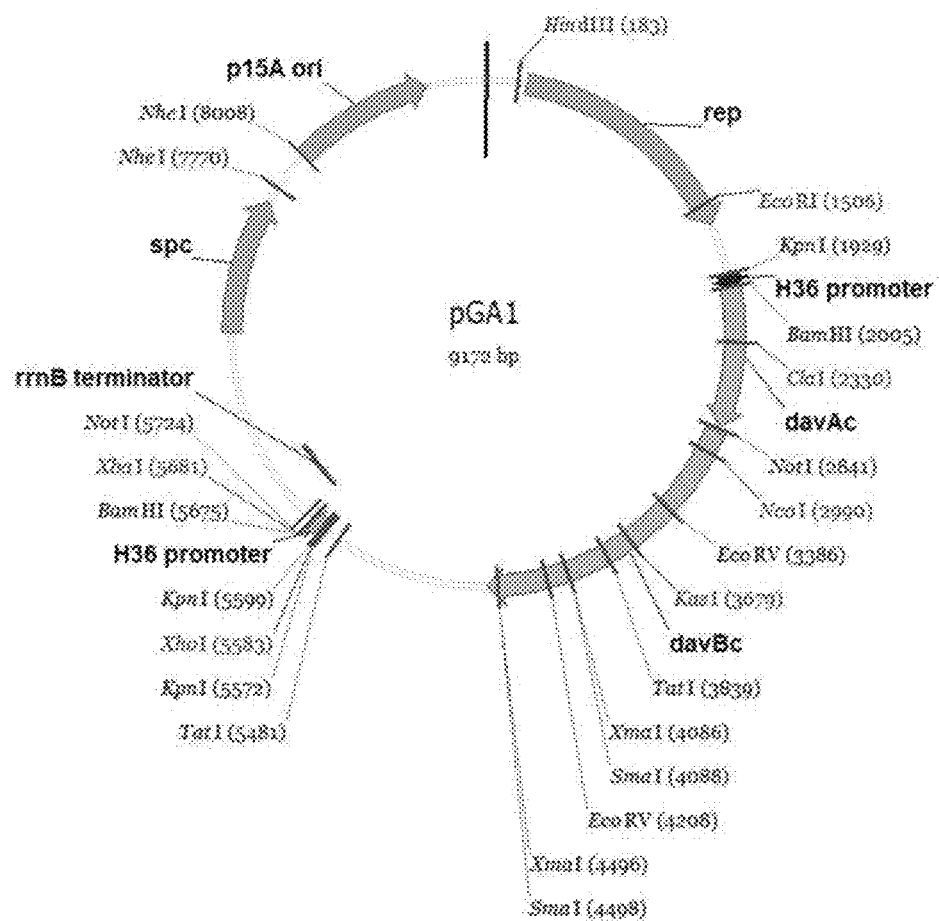
FIG. 2 shows a genetic map of a recombinant vector pGA1 containing a gene for the production of 5-α-aminovaleric acid (AVA) from lysine constructed in the present invention.

Example 2: Construction of Gene Expression Vector Involved in Production of Glutaric Acid p36davAB3 (Shin et al., *Microb. Cell Fact.* 15, 174, 2016), constructed by subjecting the chromosomal DNA sequences of the davA gene and davB gene of a *Pseudomonas putida* strain to codon optimization, was used as a template, and PCR was performed using the primer pair of SEQ ID NOS: 39 and 40 (36davAB_p208s_F and 36davAB_p208s_R) to obtain a PCR product containing the davA gene and the davB gene, and this fragment was cloned into a pCES208s vector (Lab stock) cleaved with a restriction enzyme NcoI, thereby constructing a pGA1 vector expressing a gene for converting lysine into 5-α-aminovaleric acid (AVA) (FIG. 2).

```
36davAB_p208s_F:
                                    (SEQ ID NO: 39)
GCTTCCAGCTCTGTGACGACGGTACCTCTATCTGGTGC 36davAB_p208s_R:
                                    (SEQ ID NO: 40)
CGTCCCCCGAGCGAAATTTTGGCTTAATGATGGTGATGGTGATG
```

Figure 3:
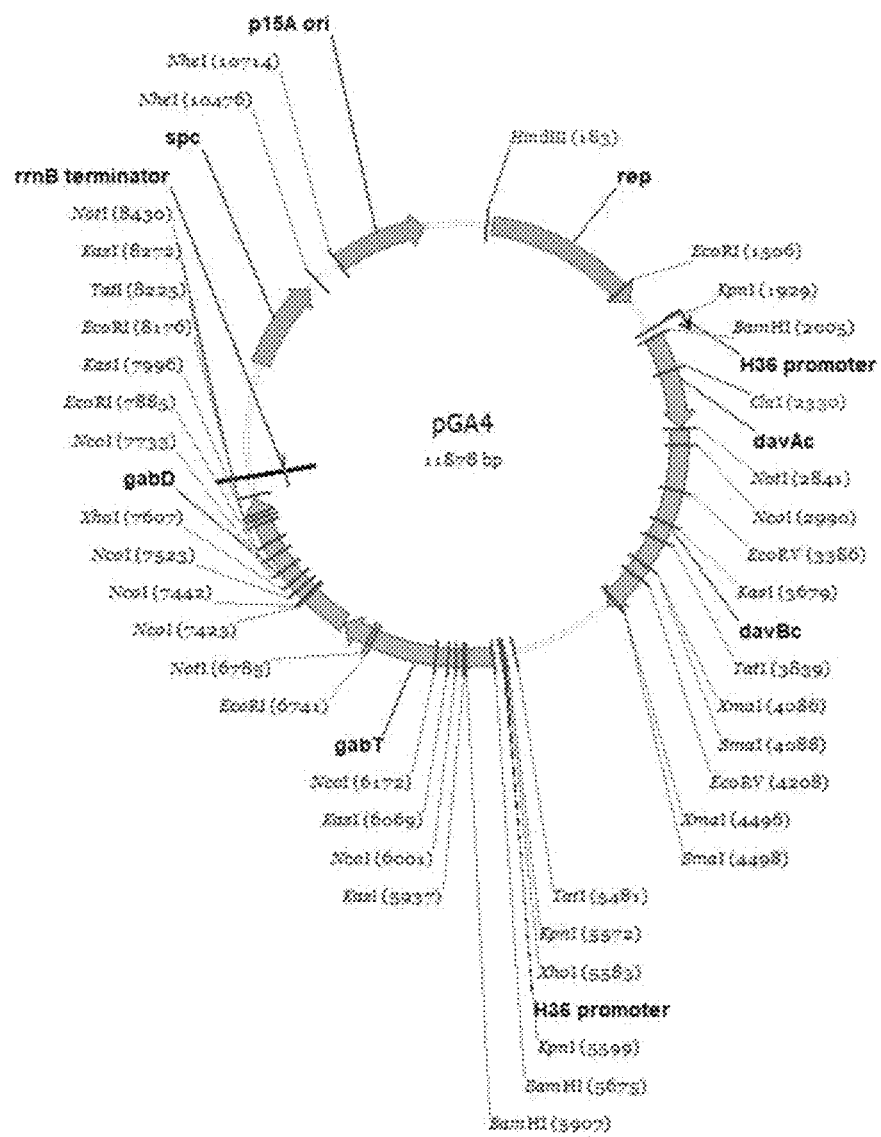
FIG. 3 shows a genetic map of a recombinant vector pGA4 containing a gene for the production of glutaric acid from 5-α-aminovaleric acid (AVA).

SEQ ID NO: 41: Codon-optimized davA gene sequence
SEQ ID NO: 42: Codon-optimized davB gene sequence Next, the chromosomes of the gabT gene and the gabD gene of the *Corynebacterium glutamicum* genome were used as a template, and PCR was performed using the primer pair of SEQ ID NOS: 43 and 44 (gabTD_p208s_F and gabTD_p208s_R) to obtain a PCR product, which was then cloned into the pGA1 vector cleaved with a restriction enzyme XbaI, thereby constructing pGA4 (FIG. 3).

```
gabTD_p208s_F:
                                       (SEQ ID NO: 43)
TAGGAGTAGCATGGGATCCTATGGAAGATCTCTCATACCGCATCC gabTD_p208s_R:
                                       (SEQ ID NO: 44)
TATAATGGCCGGCTGGGCCTTCACGGCAAAGCGAGGTAAC
```

SEQ ID NO: 45: gabT gene sequence
SEQ ID NO: 46: gabD gene sequence

Example 3: Construction of Vector Expressing Glutaric Acid Transporter Gene

The chromosomal DNA of the Ncgl2828 (ynfM) gene (SEQ ID NO: 2) of *Corynebacterium glutamicum* was used as a template, and PCR was performed using the primer pair of SEQ ID NOS: 47 and 48 (GAex5_F and GAex5_R), thus constructing a gene fragment encoding a glutaric acid transporter.

```
GAex5_F:
                                       (SEQ ID NO: 47)
TTTCACACAGGAAACAGATGATGAACTCCATGAGCCAAGC

GAex5_R:
                                       (SEQ ID NO: 48)
CCAAGCTTGGCTGCATTAATTGGCGTTGCGGGCAAG
```

Figure 4:
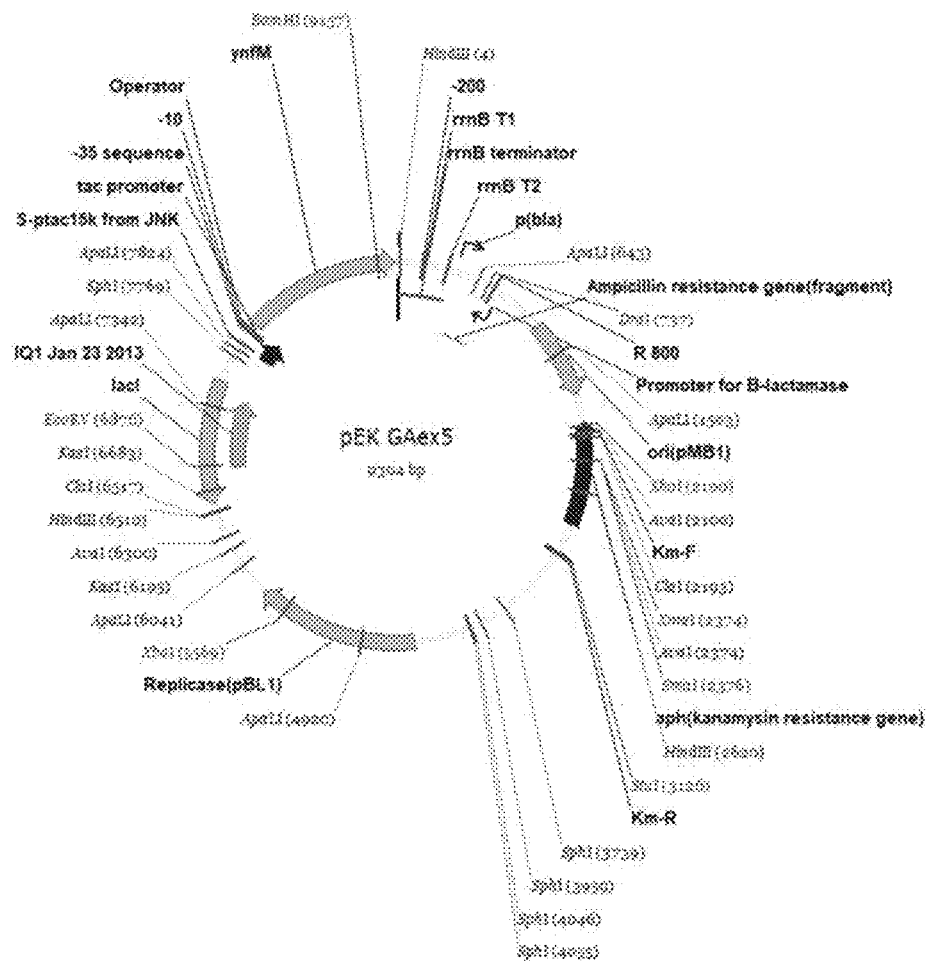
FIG. 4 shows a genetic map of a recombinant vector pEK_GAex5 for overexpression of a gene encoding a glutaric acid transporter.

The fragment thus constructed was cloned into a pEKEx1 vector cleaved with restriction enzymes EcoRI and PstI (Eikmanns B. J. et al., Gene. 102, 93-98, 1991), thereby constructing a recombinant vector pEK_GAex5 (FIG. 4).

Example 4: Confirmation of Ability to Produce Glutaric Acid in Recombinant Microorganism Introduced with Vector Expressing Glutaric Acid Transporter Gene The *Corynebacterium glutamicum* GA16 strain constructed in Example 1 was introduced with the pGA4 vector constructed in Example 2 and the pEK_GAex5 vector constructed in Example 3, and the ability thereof to produce glutaric acid was evaluated. A *Corynebacterium glutamicum* GA16 strain into which the pGA1 vector and the empty vector pEKEx1 were introduced was used as a control strain.

The mutant microorganisms constructed as described above were selected in a BHIS plate medium supplemented with 25 mg/L of kanamycin and 200 mg/L of spectinomycin (including 37 g/L of Brain Heart Infusion (BHI), 91 g/L of sorbitol, and 15 g/L of agar). The selected transformed strain was inoculated into 5 mL of a BHIS medium (including 37 g/L of Brain Heart Infusion (BHI) and 91 g/L of sorbitol) and pre-cultured at 30° C. for 18 hours. Then, 0.4 mL of the pre-cultured solution was inoculated into a 300 mL flask containing 25 mL of a glutaric acid production medium and cultured.

The composition of the glutaric acid production medium was as follows:

based on 1 liter of distilled water, 80 g/L of glucose, 1 g/L of $K_2HPO_4$, 1 g/L of $KH_2PO_4$, 1 g/L of urea, 20 g/L of $(NH_4)_2SO_4$, 10 g/L of a yeast extract, 1 g/L of $MgSO_4$, 50 mg/L of $CaCl_2$, 100 µg/L of biotin, 10 mg/L of β-alanine, 10 mg/L of thiamine HCl, 10 mg/L of nicotinic acid, 1.3 mg/L of $(NH_4)_6MoO_{24}$, 10 mg/L of $FeSO_4$, 10 mg/L of $MnSO_4$, 5 mg/L of $CuSO_4$, 10 mg/L of $ZnSO_4$, and 5 mg/L of $NiCl_2$.

The recombinant strain was cultured with shaking at 30° C. at 200 rpm for 48 hours. After completion of culture, the culture solution was centrifuged at 13,200 rpm for 10 minutes, only the supernatant was collected, and the production of glutaric acid was confirmed through HPLC analysis.

Figure 5:
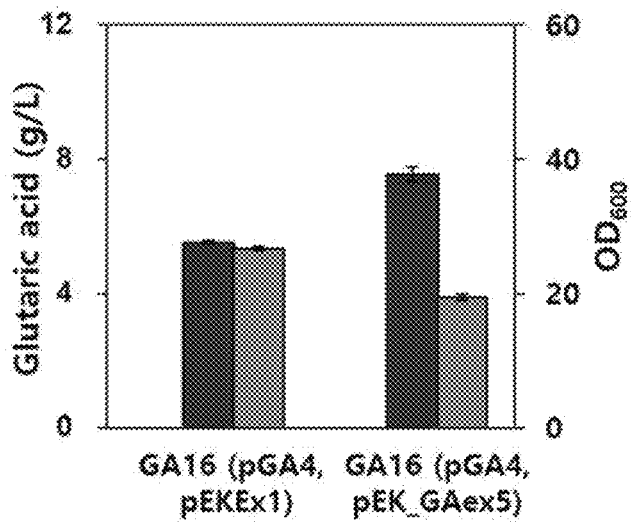
FIG. 5 shows the results of confirming the ability to produce glutaric acid in a recombinant microorganism having ability to produce glutaric acid into which the vector for overexpression of a gene encoding a glutaric acid transporter is introduced.

As a result, as shown in FIG. 5, 6.5 g/L of glutaric acid was produced in the control recombinant strain transformed with the empty vector, and 7.6 g/L of glutaric acid was produced in the mutant microorganism transformed with the pEK_GAex5 vector containing the ynfM gene, indicating that production of glutaric acid was increased due to overexpression of the glutaric acid transporter gene.

Example 5: Confirmation of Ability to Produce Glutaric Acid in Recombinant Microorganism in which Glutaric Acid Transporter Gene was Knocked Out In order to confirm that the Ncgl2828 (ynfM) gene of *Corynebacterium glutamicum* has glutaric acid transporter activity, GA16ΔynfM, which is a recombinant strain in which the above gene was knocked out from the chromosomal DNA of the *Corynebacterium glutamicum* GA16 constructed in Example 1, was constructed.

For knockout of the ynfM gene, the upstream portion, which is the homologous arm, was amplified in the *C. glutamicum* BE genome using the primer pair of SEQ ID NOS: 49 and 50, and the downstream portion was amplified in the *C. glutamicum* BE genome using the primer pair of SEQ ID NOS: 51 and 52. Then, the amplified sequences were inserted into pK19mob-sacB cleaved with BamHI and PstI through Gibson assembly, thereby constructing a final vector psacB_ynfMKO.

```
SEQ ID NO: 49:
GCTTGCATGCCTGCAATGCGAGGTCAGTTTCATCAGC

SEQ ID NO: 50:
CAGGTCCCCACAGCGCGCTTGTAATTGC

SEQ ID NO: 51:
GCGCTGTGGGGACCTGGAGTTCCACC

SEQ ID NO: 52:
AGCTCGGTACCCGGGCCACACCACAATCGAATTGGTG
```

Moreover, in order to confirm the effect of restoring the expression of the ynfM gene by introducing the pEK_GAex5 vector for overexpression of the ynfM gene and the pGA4 vector into the GA16ΔynfM strain in which the ynfM gene was knocked out, a GA16 ΔynfM(pGA4, pEK_GAex5) strain in which the recombinant microorganism subjected to gene knockout was transformed with the pEK_GAex5 vector was constructed. The recombinant strains constructed as described above were cultured under the same conditions as in Example 4, and the ability thereof to produce glutaric acid was evaluated.

As a result, as shown in FIG. 6, glutaric acid was not produced at all in the recombinant strain in which the ynfM gene was knocked out, whereas 4.6 g/L of glutaric acid was produced in the recombinant strain in which the expression of the ynfM gene was restored by introducing the recombinant vector. Therefore, it was demonstrated that the *Corynebacterium glutamicum* Ncg12828 (ynfM) gene has glutaric acid transporter activity.

Although specific embodiments of the present invention have been disclosed in detail as described above, it will be obvious to those of ordinary skill in the art that the description is merely of preferable exemplary embodiments and is not to be construed as limiting the scope of the present invention. Therefore, the substantial scope of the present invention will be defined by the appended claims and equivalents thereof.

The invention claimed is:

1. A recombinant *Corynebacterium glutamicum* that produces glutaric acid, wherein the *Corynebacterium glutamicum* is transformed with the *Corynebacterium glutamicum* ddh gene, the *Corynebacterium glutamicum* gabT gene, the *Corynebacterium glutamicum* gabD gene, the *Pseudomonas putida* davA gene and *Pseudomonas putida* davB gene,
in which the *Corynebacterium glutamicum* lysE gene is deleted, and
in which the *Corynebacterium glutamicum* ynfM gene of SEQ ID NO: 2 encoding a polypeptide having glutaric acid transporter activity is expressed under a strong heterologous promoter.

2. A method of preparing glutaric acid, comprising:
   (a) producing glutaric acid by culturing the recombinant microorganism according to claim 1; and
   (b) recovering the produced glutaric acid.

* * * * *

UNITED STATES PATENT AND TRADEMARK OFFICE
CERTIFICATE OF CORRECTION

PATENT NO. : 11,965,200 B2
APPLICATION NO. : 17/549757
DATED : April 23, 2024
INVENTOR(S) : Sang Yup Lee et al.

Page 1 of 1

It is certified that error appears in the above-identified patent and that said Letters Patent is hereby corrected as shown below:

In the Specification

Column 6, Line 34, "Agt10" should be -- λgt10 --.

Column 10, Lines 12-13,
"SEQ ID NO: 33:
CATGGGATCCATGGCTACAGTTGAAAATTTCATGACTTCC" should be
-- SEQ ID NO: 33:
CATGGGATCCATGGCTACAGTTGAAAATTTCAATGAACTTCC --.

Column 10, Lines 15-16,
"SEQ ID NO: 34:
AGTGATTCGAGCTCGGTACCCGGGGGCTTTACGCGGATCAACAC" should be
-- SEQ ID NO: 34:
AGTGAATTCGAGCTCGGTACCCGGGGGCTTTACGCGGATCAACAC --.

Signed and Sealed this
Thirty-first Day of December, 2024

Derrick Brent
*Acting Director of the United States Patent and Trademark Office*

SEQUENCE LISTING

```
<160> NUMBER OF SEQ ID NOS: 52

<210> SEQ ID NO 1
<211> LENGTH: 413
<212> TYPE: PRT
<213> ORGANISM: Artificial Sequence
<220> FEATURE:
<223> OTHER INFORMATION: ynfM

<400> SEQUENCE: 1

Met Met Asn Ser Met Ser Gln Ala Ile Asp Ser Lys Val Glu Ala His
1               5                   10                  15

Glu Gly Tyr Glu Gly Ile Glu Arg Gly Thr Arg Asn Tyr Lys Arg Ala
                20                  25                  30

Val Phe Ala Met Leu Ala Ala Gly Leu Ala Ala Phe Asn Gly Leu Tyr
            35                  40                  45

Cys Thr Gln Ala Leu Leu Pro Thr Met Thr Glu Glu Leu Gly Ile Thr
        50                  55                  60

Pro Thr Glu Ser Ala Leu Thr Val Ser Ala Thr Thr Gly Met Leu Ala
65                  70                  75                  80

Leu Cys Ile Val Pro Ala Ser Ile Leu Ser Glu Lys Phe Gly Arg Gly
                85                  90                  95

Arg Val Leu Thr Ile Ser Leu Thr Leu Ala Ile Ile Val Gly Leu Ile
                100                 105                 110

Leu Pro Leu Val Pro Asn Ile Thr Ala Leu Ile Leu Leu Arg Gly Leu
            115                 120                 125

Gln Gly Ala Leu Leu Ala Gly Thr Pro Ala Val Ala Met Thr Trp Leu
        130                 135                 140

Ser Glu Glu Ile His Pro Lys Asp Ile Gly His Ala Met Gly Ile Tyr
145                 150                 155                 160

Ile Ala Gly Asn Thr Val Gly Gly Leu Thr Gly Arg Met Ile Pro Ala
                165                 170                 175

Gly Leu Leu Glu Val Thr His Trp Gln Asn Ala Leu Leu Gly Ser Ser
                180                 185                 190

Ile Ala Ala Leu Ile Phe Gly Val Ile Met Val Val Leu Leu Pro Lys
            195                 200                 205

Gln Arg Lys Phe Gln Pro Lys Asn Ile Asn Leu Gly His Glu Val Ser
        210                 215                 220

Ala Met Ala Ala His Trp Arg Asn Pro Arg Leu Ala Leu Leu Phe Gly
225                 230                 235                 240

Thr Ala Phe Leu Gly Met Gly Thr Phe Val Ser Leu Tyr Asn Tyr Leu
                245                 250                 255

Gly Phe Arg Met Ile Asp Gln Phe Gly Leu Ser Glu Val Leu Val Gly
                260                 265                 270

Ala Val Phe Ile Met Tyr Leu Ala Gly Thr Trp Ser Ser Thr Gln Ala
            275                 280                 285

Gly Ala Leu Arg Glu Lys Ile Gly Asn Gly Gln Thr Val Ile Phe Leu
        290                 295                 300
```

```
Ser Leu Met Met Ile Ala Ser Met Ala Leu Met Gly Ile Asn Asn Leu
305                 310                 315                 320

Trp Ile Thr Leu Ile Ala Leu Phe Val Phe Thr Ala Ala Phe Phe Ala
            325                 330                 335

Leu His Ser Ser Ala Ser Gly Trp Ile Gly Ile Ala Thr Lys Asp
        340                 345                 350

Arg Ala Glu Ala Ser Ser Met Tyr Leu Phe Cys Tyr Tyr Val Gly Ser
        355                 360                 365

Ser Val Ile Gly Trp Val Ser Gly Phe Ala Phe Thr His Leu Pro Trp
370                 375                 380

Leu Ala Phe Ile Gly Trp Leu Ile Leu Leu Phe Gly Val Leu Ala
385                 390                 395                 400

Ile Cys Val Thr Leu Ala Arg Leu Ala Arg Asn Ala Asn
            405                 410
```

<210> SEQ ID NO 2
<211> LENGTH: 1242
<212> TYPE: DNA
<213> ORGANISM: Artificial Sequence
<220> FEATURE:
<223> OTHER INFORMATION: ynfM

<400> SEQUENCE: 2

```
atgatgaact ccatgagcca agcaatagat agcaaggtcg aggcacacga aggttacgaa      60
ggcatcgagc gaggaacacg caattacaag cgcgctgtgt ttgcgatgct ggccgccggt     120
cttgctgctt tcaatggtct ttattgcacg caggcattgc ttcccaccat gacggaagag     180
ttgggaatta cgcctactga gtccgcgctg acggtgtcgg cgacgactgg aatgttggcg     240
ctgtgtattg ttccggcgtc gatactttcg gagaaatttg gtcgcggtcg ggtgctgaca     300
atttcactca cgttggccat catcgtggga ttaattttgc cgcttgtccc caatatcact     360
gctctcatcc tgctcagagg tctccaaggt gcgctgcttg ctggcactcc ggcggtggcg     420
atgacctggt tgtctgagga aattcacccc aaggatattg gcacgcgat gggaatttac      480
atcgcgggaa atactgtcgg cgggctcact ggacgtatga ttccggcggg actacttgaa     540
gtaactcatt ggcaaaacgc actgctggga agttctatcg ctgcgctaat cttcggcgta     600
atcatggtgg tattgcttcc caaacagcgg aaattccagc cgaagaatat caatctgggt     660
catgaggttt ctgcgatggc tgctcattgg cggaatcctc gtttggcttt gctcttttggt    720
actgcatttt tgggcatggg tactttttgtg tcgctgtaca actatttggg tttccgcatg     780
attgatcagt ttgggctgag tgaagtgctg gttggtgcag tgttcatcat gtatctggcc     840
gggacctgga gttccaccca ggcgggtgcg ttgagggaga agattggcaa tggacaaact     900
gtcattttct tgagcctgat gatgatcgcc tcgatggctc tcatgggcat taacaatttg     960
tggatcaccc tcatcgcgct ttttgtgttc acagcagcgt ttttcgcact gcattccagt    1020
gcttcgggat ggatcggaat catcgcaacg aaggatcgcg cggaagcctc cagcatgtat    1080
ttgttctgtt attacgtggg atcctcggtg attggttggg tttctggatt cgcgtttacg    1140
catttgccgt ggtggcgtt cattggctgg ttgattctgc ttcttttttgg agtgctggcg    1200
atttgtgtga cgctggcaag gcttgcccgc aacgccaatt aa                      1242
```

<210> SEQ ID NO 3
<211> LENGTH: 41
<212> TYPE: DNA
<213> ORGANISM: Artificial Sequence

```
<220> FEATURE:
<223> OTHER INFORMATION: primer

<400> SEQUENCE: 3
gccaagcttg catgcctgca ggaatctgca gaccactcgc c                    41

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
aaggagactc gtggctaaga tcatctggac cc                              32

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
tcttagccac gagtctcctt ggttgatggg c                               31

<210> SEQ ID NO 6
<211> LENGTH: 44
<212> TYPE: DNA
<213> ORGANISM: Artificial Sequence
<220> FEATURE:
<223> OTHER INFORMATION: primer

<400> SEQUENCE: 6
attcgagctc ggtacccggg gatccgcacg catcctcgaa gacc                 44

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
gccaagcttg catgcctgca gtcgtggtct ggtccacgg                       39

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
cagaccacga catccaaacc caaccgcg                                   28

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
ggtttggatg tcgtggtctg gtccacgg                                   28
```

```
<210> SEQ ID NO 10
<211> LENGTH: 43
<212> TYPE: DNA
<213> ORGANISM: Artificial Sequence
<220> FEATURE:
<223> OTHER INFORMATION: primer

<400> SEQUENCE: 10
attcgagctc ggtacccggg gatcccatcc aaacccaacc gcg        43

<210> SEQ ID NO 11
<211> LENGTH: 39
<212> TYPE: DNA
<213> ORGANISM: Artificial Sequence
<220> FEATURE:
<223> OTHER INFORMATION: primer

<400> SEQUENCE: 11
gccaagcttg catgcctgca gtctggctgt gcgtccatg            39

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
catgggatcc atgggaatca aggttggcgt tc                    32

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
cttgattccc atggatccca tgctactcct acc                   33

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
cttaagtctc atggtacctc tatctggtgc cc                    32

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
tagaggtacc atgagactta agttgcccct cacc                  34

<210> SEQ ID NO 16
<211> LENGTH: 54
<212> TYPE: DNA
<213> ORGANISM: Artificial Sequence
<220> FEATURE:
<223> OTHER INFORMATION: primer
```

<400> SEQUENCE: 16
attcgagctc ggtacccggg gatcccttg aatattgacg ttgaggaagg aatc          54

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
gccaagcttg catgcctgca gacgaggtca cccttggcg                          39

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
catgggatcc atgagcacag gtttaacagc taagac                             36

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
acctgtgctc atggatccca tgctactcct acc                                33

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20
atggactttt aaggtacctc tatctggtgc cc                                 32

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
tagaggtacc ttaaaagtcc atgacatacg ggcttg                             36

<210> SEQ ID NO 22
<211> LENGTH: 44
<212> TYPE: DNA
<213> ORGANISM: Artificial Sequence
<220> FEATURE:
<223> OTHER INFORMATION: primer

<400> SEQUENCE: 22
attcgagctc ggtacccggg gatccccgag gcatttctcg gtcc                    44

<210> SEQ ID NO 23

```
<211> LENGTH: 39
<212> TYPE: DNA
<213> ORGANISM: Artificial Sequence
<220> FEATURE:
<223> OTHER INFORMATION: primer

<400> SEQUENCE: 23
gccaagcttg catgcctgca gggtaggctc cgcagactg                    39

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24
catgggatcc atgactgatt ttttacgcga tgacatc                      37

<210> SEQ ID NO 25
<211> LENGTH: 32
<212> TYPE: DNA
<213> ORGANISM: Artificial Sequence
<220> FEATURE:
<223> OTHER INFORMATION: primer

<400> SEQUENCE: 25
aaaatcagtc atggatccca tgctactcct ac                           32

<210> SEQ ID NO 26
<211> LENGTH: 31
<212> TYPE: DNA
<213> ORGANISM: Artificial Sequence
<220> FEATURE:
<223> OTHER INFORMATION: primer

<400> SEQUENCE: 26
gtagaagtgc ggggtacctc tatctggtgc c                            31

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
tagaggtacc ccgcacttct acagtgcttg                              30

<210> SEQ ID NO 28
<211> LENGTH: 45
<212> TYPE: DNA
<213> ORGANISM: Artificial Sequence
<220> FEATURE:
<223> OTHER INFORMATION: primer

<400> SEQUENCE: 28
attcgagctc ggtacccggg gatccctgct cttgggttgt cgttg             45

<210> SEQ ID NO 29
<211> LENGTH: 41
<212> TYPE: DNA
<213> ORGANISM: Artificial Sequence
<220> FEATURE:
<223> OTHER INFORMATION: primer

<400> SEQUENCE: 29
```

```
gccaagcttg catgcctgca gcgttcctcc gtggattcct c                          41
```

<210> SEQ ID NO 30
<211> LENGTH: 31
<212> TYPE: DNA
<213> ORGANISM: Artificial Sequence
<220> FEATURE:
<223> OTHER INFORMATION: primer

<400> SEQUENCE: 30

```
tagaggtacc tgttacatct tctccggtgc g                                     31
```

<210> SEQ ID NO 31
<211> LENGTH: 32
<212> TYPE: DNA
<213> ORGANISM: Artificial Sequence
<220> FEATURE:
<223> OTHER INFORMATION: primer

<400> SEQUENCE: 31

```
gaagatgtaa caggtacctc tatctggtgc cc                                    32
```

<210> SEQ ID NO 32
<211> LENGTH: 33
<212> TYPE: DNA
<213> ORGANISM: Artificial Sequence
<220> FEATURE:
<223> OTHER INFORMATION: primer

<400> SEQUENCE: 32

```
aactgtagcc atggatccca tgctactcct acc                                   33
```

<210> SEQ ID NO 33
<211> LENGTH: 42
<212> TYPE: DNA
<213> ORGANISM: Artificial Sequence
<220> FEATURE:
<223> OTHER INFORMATION: primer

<400> SEQUENCE: 33

```
catgggatcc atggctacag ttgaaaattt caatgaactt cc                         42
```

<210> SEQ ID NO 34
<211> LENGTH: 45
<212> TYPE: DNA
<213> ORGANISM: Artificial Sequence
<220> FEATURE:
<223> OTHER INFORMATION: primer

<400> SEQUENCE: 34

```
agtgaattcg agctcggtac ccggggggctt tacgcggatc aacac                     45
```

<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35

```
gcttgcatgc ctgcaatctg ctgcagtcag ctgcc                                 35
```

<210> SEQ ID NO 36
<211> LENGTH: 32
<212> TYPE: DNA

<213> ORGANISM: Artificial Sequence
<220> FEATURE:
<223> OTHER INFORMATION: primer

<400> SEQUENCE: 36
gtctgctttg cgacaccgga cggtggattt tc                32

<210> SEQ ID NO 37
<211> LENGTH: 37
<212> TYPE: DNA
<213> ORGANISM: Artificial Sequence
<220> FEATURE:
<223> OTHER INFORMATION: primer

<400> SEQUENCE: 37
ggtgtcgcaa agcagacctg taatgaagat ttccatg           37

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
agctcggtac ccgggcatca accatgtagg catcccg           37

<210> SEQ ID NO 39
<211> LENGTH: 38
<212> TYPE: DNA
<213> ORGANISM: Artificial Sequence
<220> FEATURE:
<223> OTHER INFORMATION: primer

<400> SEQUENCE: 39
gcttccagct ctgtgacgac ggtacctcta tctggtgc          38

<210> SEQ ID NO 40
<211> LENGTH: 44
<212> TYPE: DNA
<213> ORGANISM: Artificial Sequence
<220> FEATURE:
<223> OTHER INFORMATION: primer

<400> SEQUENCE: 40
cgtcccccga gcgaaatttt ggcttaatga tggtgatggt gatg    44

<210> SEQ ID NO 41
<211> LENGTH: 816
<212> TYPE: DNA
<213> ORGANISM: Artificial Sequence
<220> FEATURE:
<223> OTHER INFORMATION: codon optimized davA gene

<400> SEQUENCE: 41
atgcatcacc atcaccatca tcatcgcatc gcactgtacc aaggcgcacc caagccacta      60
gacgttcctg gtaaccttca acggctgcgc caccaggcgc agctggcagc tgaacgcgga     120
gctcagttgc tggtgtgccc agagatgttc ctcaccggct acaacattgg cctgccccaa     180
gtcgaacgtc tcgccgaagc cgcagatggc ccagcagcaa tgaccgtggt cgaaatcgct     240
caggctcacc gcatcgcaat tgtttacggt tacccggagc gcggtgatga cggagctatc     300
tacaactccg ttcagttgat cgatgcgcat ggacgatctc tgtcaaatta tcgcaagacg     360
cacttgttcg gtgaactcga tcgctcgatg ttctcccctg gtgcggacca cttcccagtc     420

```
gtggaactgg aaggctggaa ggttggactt cttatctgtt acgacatcga gttcccagag      480
aacgcccgtc gactagcgtt ggatggagcc gagcttatcc ttgtgcccac cgctaacatg      540
actccgtacg attttacctg ccaagtgact gtccgtgcga gggcacagga aaatcagtgc      600
tacctcgtat atgcaaacta ctgcggtgct gaagacgaga ttgaatattg tgggcaatct      660
agcattattg gaccggatgg ctccttgctc gctatggccg tcgcgatga atgccagttg      720 cttgcagagc ttgagcatga gcgggtcgtt caggggcgta cagcttttcc ttatttaacc      780
gacctccgtc aggagctgca cctgcgtaaa ggctaa                                816
```

<210> SEQ ID NO 42
<211> LENGTH: 1701
<212> TYPE: DNA
<213> ORGANISM: Artificial Sequence
<220> FEATURE:
<223> OTHER INFORMATION: codon optimized davB gene

<400> SEQUENCE: 42

```
atgaacaaga agaatcgaca ccccgccgac ggcaagaagc cgattaccat tttcggacca       60
gatttccctt ttgctttcga tgattggcta gaacacccag caggcctggg aagcattcca      120
gctgagcgcc atggagaaga ggtggctatc gtcggagctg gtatcgctgg cctcgtagcg      180
gcatacgagc tgatgaagct gggcctcaag cctgtggtgt atgaggcttc caagctcggc      240
ggccggctcc gctcccaagc cttcaatgga actgacggga tcgttgccga gctgggtggc      300
atgcgcttcc cagtgtcttc cactgccttc taccactacg tcgacaaatt gggcctggaa      360 acgaaacccct tccccaatcc tttgacccca gcttccggaa gtacggttat tgatcttgaa      420
ggacagacct attacgccga gaaacctaca gaccttccac aactgttttca tgaggttgcc      480 gacgcatggg ctgatgctct ggagtcgggt gcgcagttcg ccgatatcca gcaggcaatc      540
cgcgatcgtg atgtaccacg ccttaaggaa ttatggaaca agttggttcc actgtgggac      600
gaccgtacct tctacgactt cgtcgctacc tctcgctcct tgctaaaact gagcttttcaa     660 cacagagaag tgtttggcca ggtcggtttc ggcaccggcg gttgggattc ggacttccct      720
aacagtatgt tggaaatctt ccgcgtggtt atgaccaact gcgacgacca ccagcacctg      780
gttgttgggg gtgtgaacaa gtcccacaa ggaatctggc ccacgtgcc ggaacgttgt        840 gtgcattggc cagaagggac tagcctgagc acgctgcatg gtggcgcacc gcgtaccggt      900
gtcaagcgca ttgcccgcgc atccgatggc cgcttggcag tcacggacaa ctggggtgat      960
acccgccact attccgcagt actagctacc tgtcagacat ggttgcttac cactcaaatc     1020
gactgcgaag aatctctgtt ctcgcaaaag atgtggatgg cactggaccg gacccgctac     1080
atgcagtcgt ctaaaaccctt tgtcatggtc gacaggccgt tctggaagga taaggaccct    1140
gagaccggtc gtgacctgct gagcatgacc ctcactgatc gtctcactcg cggcacttat     1200 cttttttgata cgtaacga taaacccggg gtgatctgcc tgtcatactc atggatgtct      1260
gatgcgctga gatgctgcc acacccggtg gagaagcgcg tacagcttgc cctggatgcg     1320
ctcaagaaga tttatccgaa aaccgatatc gcaggccata tcatcggcga tccaatcacg     1380
gtttcctggg aggccgaccc ctactttctc ggcgcgttca aaggcgcgtt accgggtcat     1440
taccgctaca accagcgaat gtacgcgcac ttcatgcagc aggatatgcc ggcagagcag    1500
cgcggtattt ttattgctgg tgatgacgtg tcatggaccc ctgcctgggt tgaaggcgcg    1560
gtccagacat ctctgaacgc agtgtggggt atcatgaatc actttggtgg gcacacccac    1620
```

| | |
|---|---|
| ccagacaatc caggcccggg agatgtgttc aacgagatcg cccgatcgc cctggcagat | 1680 |
| catcaccatc accatcatta a | 1701 |

<210> SEQ ID NO 43
<211> LENGTH: 45
<212> TYPE: DNA
<213> ORGANISM: Artificial Sequence
<220> FEATURE:
<223> OTHER INFORMATION: primer

<400> SEQUENCE: 43

| | |
|---|---|
| taggagtagc atgggatcct atggaagatc tctcataccg catcc | 45 |

<210> SEQ ID NO 44
<211> LENGTH: 40
<212> TYPE: DNA
<213> ORGANISM: Artificial Sequence
<220> FEATURE:
<223> OTHER INFORMATION: primer

<400> SEQUENCE: 44

| | |
|---|---|
| tataatggcc ggctgggcct tcacggcaaa gcgaggtaac | 40 |

<210> SEQ ID NO 45
<211> LENGTH: 1347
<212> TYPE: DNA
<213> ORGANISM: Artificial Sequence
<220> FEATURE:
<223> OTHER INFORMATION: gabT gene

<400> SEQUENCE: 45

| | |
|---|---|
| atggaagatc tctcataccg catcccgcag tcgcgcaccg tggccgagca ggtgccaggg | 60 |
| ccgaagtcga aagcgctgga tgagcgtcga caagcagcag tagcacgagc acttgcaccg | 120 |
| ggtctgcctg gatacgtggt ggacgcagac ggtggcatct ggctgacgc ggacggcaac | 180 |
| cgtttcatcg acctggcctc cggcatcgcc gtgaccacgg tcgcggatc caacgcggcc | 240 |
| gtcgcgaaag ccgtcggcgc gcagctgccc gcttcaccc acacctgctt catggtctca | 300 |
| ccttatgaaa cttacgtggc catggcggag agactcaacg ccttgactcc aggcgatcac | 360 |
| gacaagaaga gcgcgctgtt taactctggc gccgaagccg tggaaaacgc cgtcaaggtg | 420 |
| gcacgcgcct acaccggcaa gggcgcggtc gtggtgttcg acaacgcgta ccacggacgg | 480 |
| accaacctca ccatggcgat gaccgcgaag aaccgcccat acaagtccgg attcggacca | 540 |
| ctagccgcag acgtctaccg tgcaccaatg tcttacccac tgcgcgacgg actgtccggc | 600 |
| ccggaagccg cagagcgcgc gatctccgtg atcgaatccc aggtcggagc cgaaaacctc | 660 |
| gcctgcgtgg tcattgaacc gatccagggc gaaggcggat tcatcgtccc cgcaccagga | 720 |
| ttcctcgcag ccatttccac ctggtgccgc gagaacgacg tggtgttcat cgccgatgaa | 780 |
| atccaatctg gcttcctgcg caccggcgac tggttcgcca cgacgcaga aggtgtgatc | 840 |
| cccgacgtca tcaccaccgc aaaaggcatc gccggcggca tgccactatc cgcagtgacc | 900 |
| ggccgcgcag aaatcatgga cgcacccggc cccggcgcgc tcggcggaac ctacggcgga | 960 |
| aaccccgttg cttgcgccgc ggcacttgca gccattgaag tgatggaaca agccgacctt | 1020 |
| aagacccgcg cgcaagaaat cgagaccatc atccgcgatg aattcgcgca gctgagtgcc | 1080 |
| ttcccggagg tcgccgaaat ccggccgg ggagcaatga tggccattga gcttatcgac | 1140 |
| gctaccggcc gccgaacgc agctttaacc gccgcagtgg ctgcgcgcgc aaaagctgaa | 1200 |
| ggtgtgctgc tgctgacttg cggcaccgat ggcaacgtca tccgcctgct gccaccactg | 1260 |

```
gtcattgcag aggacactct ccgtgatggt cttcaggtgt tagtcgcagc cctagagcgc    1320
gaaaccgcgc accagaaggt gggctaa                                        1347

<210> SEQ ID NO 46
<211> LENGTH: 1362
<212> TYPE: DNA
<213> ORGANISM: Artificial Sequence
<220> FEATURE:
<223> OTHER INFORMATION: gabD gene

<400> SEQUENCE: 46
gtgtctttga ccttcccagt aatcaacccc agcgatggct ccaccatcac cgagctagaa      60
aaccacgatt ccacccagtg gatgtccgcg ctctctgatg cagttgcagc tggtccttca     120
tgggctgcga aaactcccg cgaaagatcc gtggtactca ccgcaatctt cgaagcactg      180
accgaacgcg cccaagaact tgcagagatc atccacctgg aagctggaaa atccgttgca     240
gaagctcttg gtgaagtcgc ttatggtgca gaatacttcc gttggtttgc ggaagaagca     300
gtgcgcctgc ccggccgcta cggacagtca ccttccggaa tcggtcacat cgccgtcacc     360
cgcgcacccg tgggaccagt gctggcgatc accccatgga atttccccat cgccatggcc     420
acccgcaaaa tcgccccagc cctggccgct ggttgccccg tgttggtgaa acctgcttcc     480
gaaaccccac tgaccatggt caaagtgggg gagatcatcg cctccgtctt tgataccttt     540
aatatcccgc agggcttggt ctcaatcatc accaccactc gagatgcaga gctatcggca     600
gaactcatgg ctgatcctcg cttggctaaa gtcaccttca ctggatcaac caacgtggga     660
cgcatcctgg tccgccaatc cgcggaccga ctgctgcgca cctccatgga actcggcgga     720
aatgcagctt ttgttatcga cgaagccgca gacctgacg aagccgtatc cggtgccatc      780
gccgcaaaac tccgcaacgc cggccaagta tgcatcgcag ctaaccgttt cttggttcat     840
gaatcccgcg ctgccgaatt cacctcaaag ctggcgacag ccatgcagaa cactcccatt     900
gggccggtga tttctgcccg ccaacgcgac cggatcgcag cactagtgga tgaagccatc     960
accgacggcg cccgcctcat catcggtggg gaggtccccg acggctccgg cttcttctat    1020
ccagccacca tcttggccga tgtccctgca cagtcacgga ttgtgcatga ggaaatcttc    1080
ggacctgtgg ccaccattgc cactttcacc gacttggccg aaggcgttgc acaagcaaat    1140
tccaccgaat tcggcctcgc agcctacgga ttcagcaaca atgtgaaagc aacacagtac    1200
atggcggaac acttggaagc cggaatggtc ggaatcaaca gaggcgccat ctctgaccca    1260
gcagcacctt tggcggcat cggacaatcc ggcttcggca gagaaggcgg aaccgaagga     1320
atcgaagaat atctctccgt gcgttacctc gctttgccgt ga                       1362

<210> SEQ ID NO 47
<211> LENGTH: 40
<212> TYPE: DNA
<213> ORGANISM: Artificial Sequence
<220> FEATURE:
<223> OTHER INFORMATION: primer

<400> SEQUENCE: 47
tttcacacag gaaacagatg atgaactcca tgagccaagc                            40

<210> SEQ ID NO 48
<211> LENGTH: 36
<212> TYPE: DNA
<213> ORGANISM: Artificial Sequence
<220> FEATURE:
```

```
<223> OTHER INFORMATION: primer

<400> SEQUENCE: 48
ccaagcttgg ctgcattaat tggcgttgcg ggcaag                              36

<210> SEQ ID NO 49
<211> LENGTH: 37
<212> TYPE: DNA
<213> ORGANISM: Artificial Sequence
<220> FEATURE:
<223> OTHER INFORMATION: primer

<400> SEQUENCE: 49
gcttgcatgc ctgcaatgcg aggtcagttt catcagc                             37

<210> SEQ ID NO 50
<211> LENGTH: 28
<212> TYPE: DNA
<213> ORGANISM: Artificial Sequence
<220> FEATURE:
<223> OTHER INFORMATION: primer

<400> SEQUENCE: 50
caggtcccca cagcgcgctt gtaattgc                                       28

<210> SEQ ID NO 51
<211> LENGTH: 26
<212> TYPE: DNA
<213> ORGANISM: Artificial Sequence
<220> FEATURE:
<223> OTHER INFORMATION: primer

<400> SEQUENCE: 51
gcgctgtggg gacctggagt tccacc                                         26

<210> SEQ ID NO 52
<211> LENGTH: 37
<212> TYPE: DNA
<213> ORGANISM: Artificial Sequence
<220> FEATURE:
<223> OTHER INFORMATION: primer

<400> SEQUENCE: 52
agctcggtac ccgggccaca ccacaatcga attggtg                             37
```